United States Patent [19]
Aikins et al.

[11] Patent Number: 5,659,087
[45] Date of Patent: Aug. 19, 1997

[54] DIARYLVINYL SULFOXIDES

[75] Inventors: James A. Aikins; Tony Y. Zhang, both of Indianapolis, Ind.

[73] Assignee: Eli Lilly and Company, Indianapolis, Ind.

[21] Appl. No.: 478,706

[22] Filed: Jun. 7, 1995

[51] Int. Cl.$^6$ .................... C07C 315/00; C07C 317/00
[52] U.S. Cl. ..................... 568/27; 568/36; 568/37
[58] Field of Search .................... 568/27, 37, 36

[56] References Cited

PUBLICATIONS

Porskamp et al. Journal Org. Chem., 49(2), pp. 263–268 1984.
Dodson et al., Journal Org. Chem., 36(18), pp. 2698–2703 1971.
Campaigne and Cline, "A New Synthesis of Thiophenes and Condensed Thiophenes by Ring Closure of Disulfides", *J. Org. Chem.*, 21, 39–44 (1956).
Campaigne, "Thiophenes and their Benzo Derivatives: (III) Synthesis and Applications", in Comprehensive Heterocyclic Chemistry, vol. 4, Part 3, 863–894 (1984).
Ando, "Prolysis of Styryl Sulphoxides and Sulphides. Formation of Benzothiophen Derivatives via Intramolecular Cyclization of Thiyl Radicals", *J. Chem. Soc., Chem. Comm.*, 704–5 (1975).
Shelton and Davis, "t–Butylsulfenic Acid", *J. Am. Chem. Soc.*, 89(3), 718–19 (1967).
Mazzanti et al., "Intramolecular Trapping Reactions of Vinylsulfenic Acid Tautomers of Enethiolisable Sulfines", *J. Chem. Soc., Perkin. Trans. I*, 3299–3304 (1994).
Mukaiyama and Saigo, "A Convenient Method for the Preparation of Vinyl Sulfides from Carbonyl Compounds by Using TiCl$_4$", *Chem Letters*, 479–482 (1973).
Kodama et al., "Attractive Interaction between Aliphatic and Aromatic Systems", *Tetrahedron Letters*, 2105–08 (1977).
Casey and Manage, "Stereoselective Conjugate Additions of Benzyl Sulphoxides to α,β–Unsaturated Esters", *Tetrahedron Letters*, 30(49), 6919–22 (1989).
Casey et al., "Stereoselective Conjugate Additions of Sulphoxide Stabilised Carbanions to α,β–Unsaturated Esters", *Tetrahedron Letters*, 29(45), 5821–24 (1988).
Davis et al., "Chemistry of Sulfenic Acids. 1. Synthesis of Trimethylsilyl Arenesulfenates (Arenesulfenic Acids)", *J. Org. Chem.*, 45, 1650–53 (1980).
Davis and Friedman, "Trimethylsilyl 2–Nitrobenzenesulfenate (2–Nitrobenzensulfenic Acid)", *J. Org. Chem.*, 41(5), 897–898 (1976).
Barton and Zika, "Adducts of Acetylenes and Sulfur Dichloride", *J. Org. Chem.*, 35, 1729–33 (1970).
Guindon et al., "Direct Synthesis of Thioethers from Thiols and Alcohols", *J. Org. Chem.*, 48, 1357–59 (1983).
Pyne and Boche, "Stereoselective Reactions of Lithium and Zinc tert–Butyl Phenylmethyl Sulfoxide with Carbonyl Compounds and Imines", *J. Org. Chem.*, 54, 2663–67 (1989).

Primary Examiner—John C. Bleutoe
Assistant Examiner—Randy Gulakowski
Attorney, Agent, or Firm—Janelle D. Strode; James P. Leeds; David E. Boone

[57] ABSTRACT

The present invention is directed to new diarylvinyl sulfoxides.

15 Claims, No Drawings

5,659,087

DIARYLVINYL SULFOXIDES

BACKGROUND OF THE INVENTION

The present invention is directed to new diarylvinyl sulfoxides. These compounds are useful for the synthesis of benzo[b]thiophenes.

Benzo[b]thiophenes have been prepared by a number of different synthetic routes. One of the most widely used methods is the oxidative cyclization of o-mercaptocinnamic acids. This route is limited to the preparation of benzo[b]thiophene-2-carboxylates. 2-Phenylbenzo[b]thiophenes are prepared by acid-catalyzed cyclization of 2-phenylthioacetaldehyde dialkyl acetals. Unsubstituted benzo[b]thiophenes are prepared by catalytic condensation of styrene and sulfur. 3-Substituted benzo[b]thiophenes are prepared by acid-catalyzed cyclization of arylthiomethyl ketones; however, this route is limited to the preparation of 3-alkylbenzo[b]thiophenes. See Campaigne, "Thiophenes and their Benzo Derivatives: (iii) Synthesis and Applications," in *Comprehensive Heterocyclic Chemistry* (Katritzky and Rees, eds.), Volume IV, Part III, 863–934 (1984). 3-Chloro-2-phenylbenzo[b]thiophene is prepared by the reaction of diphenylacetylene with sulfur dichloride. Barton and Zika, *J. Org. Chem.*, 35, 1729–1733 (1970). Benzo[b]thiophenes have also been prepared by pyrolysis of styryl sulfoxides. However, low yields and extremely high temperatures make this route unsuitable for production-scale syntheses. See Ando, *J. Chem. Soc., Chem. Comm.*, 704–705 (1975).

The preparation of 6-hydroxy-2-(4-hydroxyphenyl)benzo[b]thiophenes was described in U.S. Pat. Nos. 4,133,814 and 4,380,635. One process described in these patents is the acid-catalyzed intramolecular cyclization/rearrangement of α-(3-methoxyphenylthio)-4-methoxyacetophenone. The reaction of this starting compound in neat polyphosphoric acid at about 85° C. to about 90° C. gives an approximate 3:1 mixture of two regioisomeric products: 6-methoxy-2-(4-methoxyphenyl)benzo[b]thiophene and 4-methoxy-2-(4-methoxyphenyl)benzo[b]thiophene. These isomeric benzo[b]thiophenes co-precipitate from the reaction mixture, producing a mixture containing both compounds. To obtain a single regioisomer, the regioisomers must be separated, such as by chromatography or fractional crystallization. Therefore, there currently exists a need for an efficient and regiospecific synthesis of 2-arylbenzo[b]thiophenes from readily available starting materials. The compounds of the present invention are useful as intermediates in an efficient and regiospecific synthesis of 2-arylbenzo[b]thiophenes.

SUMMARY OF THE INVENTION

The present invention is directed to novel diarylvinyl sulfoxides. In particular, the present invention is directed to a compound of the formula

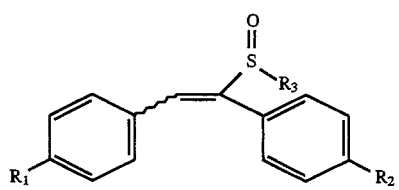

II wherein:

$R_1$ is hydrogen, $C_1$-$C_4$ alkoxy, arylalkoxy, halo, or amino;
$R_2$ is hydrogen, $C_1$-$C_4$ alkoxy, arylalkoxy, halo, or amino; and $R_3$ is a thermally-labile or acid-labile $C_2$-$C_{10}$ alkyl, $C_4$-$C_{10}$ alkenyl, or aryl($C_1$-$C_{10}$ alkyl) group. Thus, the present invention includes individually the E and Z isomers, or mixtures thereof, of the formula II compounds. These E and Z regioisomers are represented by the following structures:

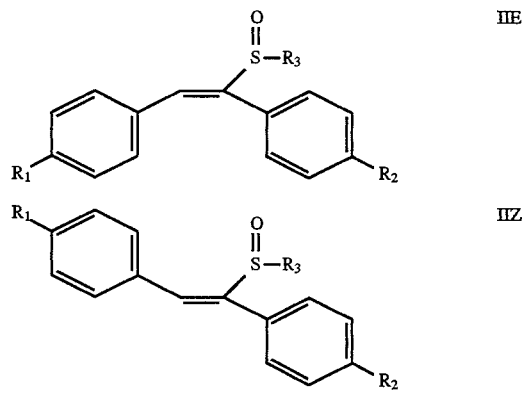

Another aspect of the present invention is a process for the synthesis of a compound of the formula

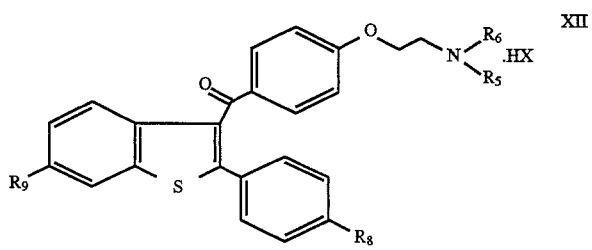

XII wherein:

$R_8$ is hydrogen, halo, amino, or hydroxyl;

$R_9$ is hydrogen, halo, amino, or hydroxyl;

$R_5$ and $R_6$ are independently $C_1$-$C_4$ alkyl, or $R_5$ and $R_6$ together with the adjacent nitrogen atom form a heterocyclic ring selected from the group consisting of pyrrolidino, piperidino, hexamethyleneimino, and morpholino; and HX is HCl or HBr;

comprising the steps of:

(a) cyclizing in the presence of an acid catalyst a compound of the formula

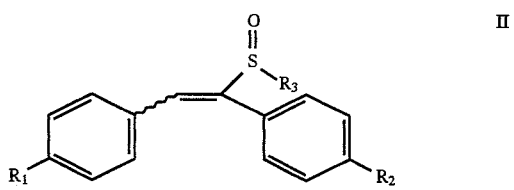

II wherein:

$R_1$ is hydrogen, $C_1$-$C_4$ alkoxy, arylalkoxy, halo, or amino;

$R_2$ is hydrogen, $C_1$-$C_4$ alkoxy, arylalkoxy, halo, or amino; and $R_3$ is a thermally-labile or acid-labile $C_2$-$C_{10}$ alkyl, $C_4$-$C_{10}$ alkenyl, or aryl($C_1$-$C_{10}$ alkyl) group to prepare a benzothiophene compound of the formula

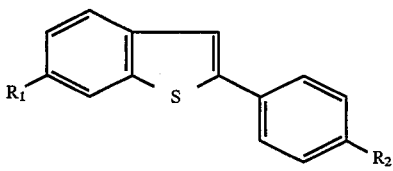

wherein $R_1$ and $R_2$ are as defined above;

(b) acylating said benzothiophene compound with an acylating agent of the formula

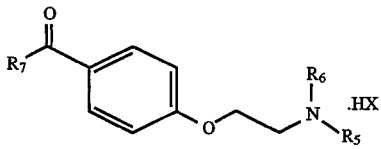

wherein:

$R_5$, $R_6$, and HX are as defined previously; and $R_7$ is chloro, bromo, or hydroxyl; in the presence of $BX'_3$, wherein $X'$ is chloro or bromo;

(c) when $R_1$ and/or $R_2$ is $C_1$–$C_4$ alkoxy or arylalkoxy, dealkylating one or more phenolic groups of the acylation product of step (b) by reacting with additional $BX'_3$, wherein $X'$ is as defined above; and (d) isolating the formula XII compound.

DETAILED DESCRIPTION OF THE INVENTION

The term "acid catalyst" represents a Lewis acid or a Brønsted acid. Representative Lewis acids are zinc chloride, zinc iodide, aluminum chloride, and aluminum bromide. Representative Brønsted acids include: inorganic acids, such as sulfuric and phosphoric acids; carboxylic acids, such as acetic and trifluorocetic acids; sulfonic acids, such as methanesulfonic, benzenesulfonic, 1-naphthalenesulfonic, 1-butanesulfonic, ethanesulfonic, 4-ethylbenzenesulfonic, 1-hexanesulfonic, 1,5-naphthalenedisulfonic, 1-octanesulfonic, camphorsulfonic, trifluoromethanesulfonic, and p-toluenesulfonic acids; and polymeric arylsulfonic acids, such as Nafion®, Amberlyst®, or Amberlite®. The preferred acids for use in catalyzing the processes of the present invention are sulfonic or polymeric sulfonic acids. More preferably, the acid catalysts are sulfonic acids, such as methanesulfonic acid, benezenesulfonic acid, camphorsulfonic acid, and p-toluenesulfonic acid. The most preferred acid catalyst is p-toluenesulfonic acid.

The term "$C_1$–$C_4$ alkoxy" represents groups such as methoxy, ethoxy, n-propoxy, isopropoxy, n-butoxy, t-butoxy, and like groups. The term "halo" refers to fluoro, chloro, bromo, or iodo groups.

The term "$C_1$–$C_6$ alkyl" represents a straight or branched alkyl chain having from one to six carbon atoms. Typical $C_1$–$C_6$ alkyl groups include methyl, ethyl, n-propyl, isopropyl, n-butyl, isobutyl, sec-butyl, t-butyl, n-pentyl, isopentyl, n-hexyl, 2-methylpentyl, and the like. The term "$C_1$–$C_4$ alkyl" represents a straight or branched alkyl chain having from one to four carbon atoms, and includes methyl, ethyl, n-propyl, isopropyl, n-butyl, sec-butyl, i-butyl, and t-butyl.

The term "aryl" represents groups such as phenyl and substituted phenyl. The term "substituted phenyl" represents a phenyl group substituted with one or more moieties chosen from the group consisting of halo, hydroxy, nitro, $C_1$–$C_4$ alkyl, $C_1$–$C_4$ alkoxy, trichloromethyl, and trifluoromethyl. Examples of a substituted phenyl group include 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl, 4-hydroxyphenyl, 3-hydroxyphenyl, 2,4-dihydroxyphenyl, 3-nitrophenyl, 4-nitrophenyl, 2,4-dinitrophenyl, 4-methylphenyl, 4-ethylphenyl, 4-methoxyphenyl, 4-propylphenyl, 4-n-butylphenyl, 4-t-butylphenyl, 3-fluoro-2-methylphenyl, 2,3-difluorophenyl, 2,6-difluorophenyl, 2,6-dimethylphenyl, 2-fluoro-5-methylphenyl, 2,4,6-trifluorophenyl, 2-trifluoromethylphenyl, 2-chloro-5-trifluoromethylphenyl, 3,5-bis(trifluoromethyl)phenyl, 2-methoxyphenyl, 3-methoxyphenyl, 3,5-dimethoxyphenyl, 4-hydroxy-3-methylphenyl, 3,5-dimethyl, 4-hydroxyphenyl, 2-methyl-4-nitrophenyl, 4-methoxy-2-nitrophenyl, and the like.

The term "arylalkyl" represents a $C_1$–$C_4$ alkyl group bearing one or more aryl groups. Representatives of this group include benzyl, o-nitrobenzyl, p-nitrobenzyl, p-halobenzyl (such as p-chlorobenzyl, p-bromobenzyl, p-iodobenzyl), 1-phenylethyl, 2-phenylethyl, 3-phenylpropyl, 4-phenylbutyl, 2-methyl-2-phenylpropyl, (2,6-dichlorophenyl)methyl, bis(2,6-dichlorophenyl) methyl, (4-hydroxyphenyl)methyl, (2,4-dinitrophenyl) methyl, diphenylmethyl, triphenylmethyl, (p-methoxyphenyl)diphenylmethyl, bis(p-methoxyphenyl) methyl, bis(2-nitrophenyl)methyl, and the like.

The term "arylalkoxy" represents a $C_1$–$C_4$ alkoxy group bearing one or more aryl groups. Representatives of this group include benzyloxy, o-nitrobenzyloxy, p-nitrobenzyloxy, p-halobenzyloxy (such as p-chlorobenzyloxy, p-bromobenzyloxy, p-iodobenzyloxy), 1-phenylethoxy, 2-phenylethoxy, 3-phenylpropoxy, 4-phenylbutoxly, 2-methyl-2-phenylpropoxy, (2,6-dichlorophenyl)methoxy, bis(2,6-dichlorophenyl)methoxy, (4-hydroxyphenyl)methoxy, (2,4-dinitrophenyl)methoxy, diphenylmethoxy, triphenylmethoxy, (p-methoxyphenyl) diphenylmethoxy, bis(p-methoxyphenyl)methoxy, bis(2-nitrophenyl)methoxy, and the like.

The term "thermally-labile or acid-labile $C_2$–$C_{10}$ alkyl, $C_4$–$C_{10}$ alkenyl, or aryl($C_1$–$C_{10}$ alkyl) group" represents a group that is readily removed from the sulfoxide (SO) group under heating or by treatment with the acid catalyst. The thermally-labile or acid-labile $C_2$–$C_{10}$ alkyl groups are straight or branched alkyl chains having from two to ten carbon atoms and having at least one beta-hydrogen atom. Representative thermally-labile or acid-labile $C_2$–$C_{10}$ alkyl groups include ethyl, n-propyl, i-propyl, 1,1-dimethylpropyl, n-butyl, sec-butyl, t-butyl, 1,1-dimethylbutyl, 2-methylbutyl, 3-methylbutyl, 1-methylbutyl, 1,2-dimethylbutyl, 1,3-dimethylbutyl, 2,4-dimethylbutyl, 3,3-dimethylbutyl, n-pentyl, 1-methylpentyl, 2-methylpentyl, 3-methylpentyl, 4-methylpentyl, n-hexyl, and the like. The thermally-labile or acid-labile $C_4$–$C_{10}$ alkenyl groups are straight or branched alkenyl chains having from four to ten carbon atoms, at least one site of unsaturation, and either a beta-hydrogen or delta-hydrogen atom. Representative thermally-labile or acid-labile $C_4$–$C_{10}$ alkenyl groups include 2-butenyl, 3-butenyl, 2-methyl-2-butenyl, 3-methyl-2-butenyl, 2-methyl-3-butenyl, 2-pentenyl, 3-pentenyl, 4-pentenyl, 2-methyl-2-pentenyl, 3-methyl-2-pentenyl, 4-methyl-2-pentenyl, 2-methyl-3-pentenyl, 3-methyl-3-pentenyl, 4-methyl-3-pentenyl, 2-methyl-4-pentenyl, 3-methyl-4-pentenyl, 4-methyl-4-pentenyl, 2-hexenyl, 3-hexenyl, 4-hexenyl, 5-hexenyl, and the like. The term thermally-labile or acid-labile aryl ($C_1$–$C_{10}$ alkyl) represents thermally-labile or acid-labile $C_2$–$C_{10}$ alkyl groups additionally containing one or more aryl groups and aryl-substituted methyl groups. Representative aryl($C_1$–$C_{10}$ alkyl) groups include benzyl, diphenylmethyl, triphenylmethyl, p-methoxybenzyl, 2-phenylethyl, 2-phenyl-propyl, 3-phenylpropyl, and the like. The term "thermally-labile or acid-labile $C_2$–$C_{10}$ alkyl, $C_4$–$C_{10}$ alkenyl, or aryl($C_1$–$C_{10}$ alkyl) group having a tertiary carbon adjacent to the sulfur atom" includes, but is not limited to, such groups as t-butyl, 1,1-dimethylpropyl, 1,1-dimethylbutyl, 1-ethyl-1-methylpropyl, 1,1-dimethylpentyl, 1-ethyl-1-methylbutyl, 1,1-diethylpropyl, 1,1-dimethylhexyl, triphenylmethyl, and the like.

The term "acid chloride" includes acyl chlorides, such as acetyl chloride and benzoyl chloride; sulfonyl chlorides, such as methanesulfonyl chloride, benzenesulfonyl chloride, 1-butanesulfonyl chloride, ethanesulfonyl chloride, isopropylsulfonyl chloride, and p-toluenesulfonyl chloride; alkoxycarbonyl chlorides, such as methoxycarbonyl chloride and benzyloxycarbonyl chloride; and dialkylaminocarbonyl chlorides, such as N,N-dimethylaminocarbonyl chloride. Preferably the acid chloride is a sulfonyl chloride. More preferably, the acid chloride is methanesulfonyl chloride.

The compounds of the present invention can be prepared by a number of routes. One method for preparing the formula II compounds is shown in Scheme 1.

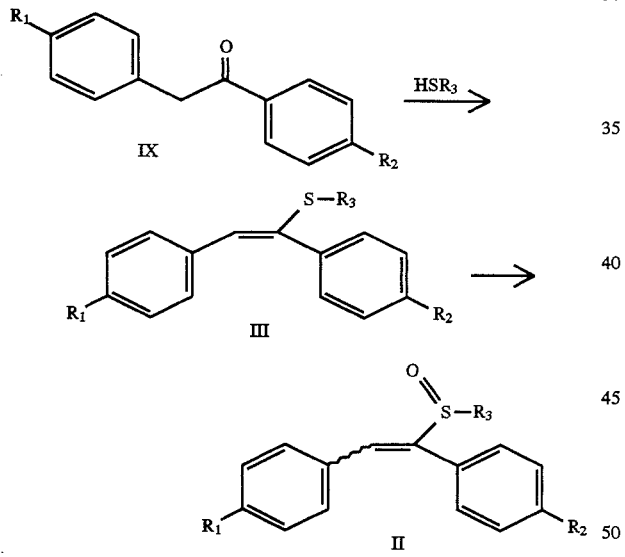

Generally, a formula IX compound is converted to a styryl sulfide by reaction with a mercaptan of the formula $HSR_3$ in the presence of a Lewis acid. The formula III compound is then oxidized to a styryl sulfoxide, a compound of formula II compound.

More specifically, a formula IX compound, wherein $R_1$ and $R_2$ are as defined above, is treated with a Lewis acid, such as titanium(IV) chloride. This reaction is carried out in an anhydrous organic solvent, such as dry tetrahydrofuran, at a temperature of about 0° C. to about 35° C. After about fifteen minutes to about one hour, the reaction mixture is treated with an amine base and a mercaptan of the formula $HSR_3$, where $R_3$ is as defined above. Preferably, the mercaptan and amine base are added as a solution in the reaction solvent. A representative amine base is triethylamine. After the addition of the mercaptan and amine base, the reaction is generally heated to a temperature of about 35° C. to about 65° C., preferably at about 50° C. The products of this reaction can be purified using techniques well known in the chemical arts, such as by crystallization or chromatography.

The formula III compound, where $R_1$, $R_2$, and $R_3$ are as defined above, is then oxidized to produce the formula II compounds. Suitable oxidizing agents for this reaction are peracids, such as peracetic acid and m-chloroperoxybenzoic acid, and hydrogen peroxide. This oxidation reaction is typically run in an organic solvent, such as toluene, methylene chloride, chloroform, or carbon tetrachloride. When a peracid is used as the oxidant, the reaction is generally carried out at a temperature of about –30° C. to about 15° C., preferably at about –20° C. The products of the reaction are easily purified by recrystallization. When $R_3$ is t-butyl, the crystalline product of this reaction sequence is the E regioisomer of formula II.

When $R_3$ has a tertiary carbon adjacent to the sulfur atom, the Z regioisomer of the formula II compounds can be prepared selectively by a second route as shown in Scheme II.

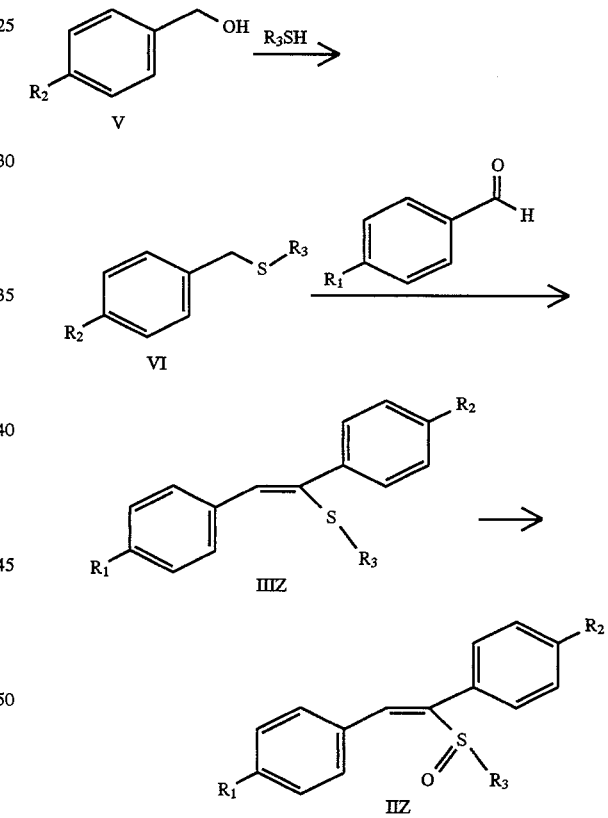

Generally, a benzyl alcohol, a formula V compound, is reacted with a mercaptan of the formula $R_3SH$ to produce a benzyl sulfide, a formula VI compound. This benzyl sulfide is reacted with a strong base, forming a benzylic anion, which is condensed with a benzaldehyde. This condensation product is reacted with an acid chloride and the resulting intermediate ester treated with a second strong base to produce a styryl sulfide, a formula IIIZ compound. This styryl sulfide is then oxidized with an oxidizing agent to produce the formula IIZ compound.

The first step in the synthesis of the Z styryl sulfoxide compounds is the conversion of a benzyl alcohol to a benzyl sulfide, formula VI compound. The reaction of the formula V compound, where $R_2$ is as defined above, with a mercaptan of the formula $R_3SH$, wherein $R_3$ is a thermally-labile or acid-labile $C_2$–$C_{10}$ alkyl, $C_4$–$C_{10}$ alkenyl, or aryl($C_1$–$C_{10}$ alkyl) group having a tertiary carbon atom adjacent to the sulfur atom, in the presence of a Lewis acid produces the benzyl sulfide, a formula VI compound. Suitable Lewis acids for this transformation are zinc bromide, zinc chloride, zinc iodide, ferric chloride, titanium(IV) chloride, aluminum trichloride, and aluminum tribromide, preferably zinc iodide. The reaction is generally carried out in an organic solvent, such as 1,2-dichloroethane or methylene chloride. When the reaction is carried out at room temperature, the reaction is complete after about 18 hours.

The benzyl sulfide is reacted with a strong base to form a benzylic anion. Suitable strong bases for this reaction include metal alkoxides, such as sodium methoxide, sodium ethoxide, lithium ethoxide, lithium t-butoxide, and potassium t-butoxide; sodium hydride; and alkyllithiums, such as n-butyllithium, t-butyllithium, sec-butyllithium, and methyllithium. The preferred strong base for this reaction is n-butyllithium. The preferred solvent for this reaction is dry tetrahydrofuran. When n-butyllithium is used as the strong base, the reaction is carried out at a temperature of about –35° C. to about –15° C.

The benzylic anion is condensed with a benzaldehyde to prepare an intermediate condensation product. The benzaldehyde has the general formula $R_1(C_6H_4)CHO$, wherein $R_1$ is hydrogen, $C_1$–$C_4$ alkoxy, arylalkoxy, halo, or amino. Preferably, the benzylic anion is prepared and the condensation product is formed in situ by adding the benzaldehyde to the cold solution of the benzylic anion.

The condensation product is treated with an acid chloride to produce an intermediate ester. Representative acid chlorides include acyl chlorides, such as acetyl chloride and benzoyl chloride; sulfonyl chlorides, such as methanesulfonyl chloride, benzenesulfonyl chloride, 1-butanesulfonyl chloride, ethanesulfonyl chloride, isopropylsulfonyl chloride, and p-toluenesulfonyl chloride; alkoxycarbonyl chlorides, such as methoxycarbonyl chloride and benzyloxycarbonyl chloride; and dialkylaminocarbonyl chlorides, such as N,N-dimethylaminocarbonyl chloride; preferably a sulfonyl chloride. Preferably, methanesulfonyl chloride is added to the reaction mixture shortly after formation of the condensation product.

This intermediate ester is reacted with a second strong base to produce a styryl sulfide, a formula IIIZ compound where $R_1$, $R_2$, and $R_3$ are as defined above. Suitable strong bases for this reaction include metal alkoxides, such as sodium methoxide, sodium ethoxide, lithium ethoxide, lithium t-butoxide, and potassium t-butoxide; sodium hydride; alkyllithiums, such as n-butyllithium, t-butyllithium, sec-butyllithium, and methyllithium; and metal amides, such as sodium amide, magnesium diisopropylamide, and lithium diisopropylamide. The preferred strong base for this reaction is potassium t-butoxide. Generally, this reaction is carried out at about 15° C. to about room temperature, preferably at room temperature.

The styryl sulfide is oxidized to prepare the corresponding styryl sulfoxide. Suitable oxidizing agents for this reaction are peracids, such as peracetic acid and m-chloroperoxybenzoic acid; organic peroxides, such as t-butyl peroxide; and hydrogen peroxide. Preferably the oxidizing agent is peracetic acid. This oxidation is typically carried out in an organic solvent, such as toluene, benzene, xylene, methanol, ethanol, methylacetate, ethylacetate, methylene chloride, 1,2-dichloroethane, or chloroform; preferably methylene chloride. This oxidation can be carried out at a temperature of about –40° C. to about 0° C.

Alternatively, when $R_3$ has a tertiary carbon adjacent to the sulfur atom, the benzyl sulfide intermediate (formula VI compound) can be used to produce a mixture of E and Z isomers of the styryl sulfoxides, the formula II compounds. This synthesis is outlined is Scheme 3.

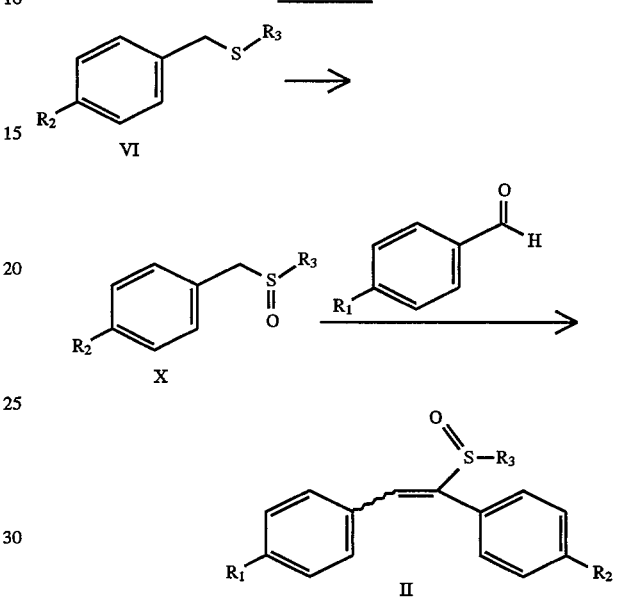

The benzyl sulfide, prepared as described above, is oxidized to produce the corresponding benzyl sulfoxide. This benzyl sulfoxide is reacted with a strong base, and the resulting anion condensed with a benzaldehyde. The condensation product is reacted with an acid chloride and the resulting intermediate ester reacted with a second strong base to produce the styryl sulfoxide.

The benzyl sulfide, the formula VI compound, wherein $R_2$ is as defined above and $R_3$ is a thermally-labile or acid-labile $C_2$–$C_{10}$ alkyl, $C_4$–$C_{10}$ alkenyl, or aryl($C_1$–$C_{10}$ alkyl) group having a tertiary carbon atom adjacent to the sulfur atom, is oxidized to produce the corresponding benzyl sulfoxide, formula X compound. Suitable oxidizing agents for this reaction are peracids, such as peracetic acid and m-chloroperoxybenzoic acid; organic peroxides, such as t-butyl peroxide; and hydrogen peroxide. Preferably the oxidizing agent is peracetic acid. This oxidation is typically carried out in an organic solvent, such as toluene, benzene, xylene, methanol, ethanol, methylacetate, ethylacetate, methylene chloride, 1,2-dichloroethane, or chloroform; preferably at a temperature of about –30° C. to about 5° C.

The benzyl sulfoxide, formula X compound wherein $R_2$ and $R_3$ are as defined above, is reacted with a strong base to produce a benzylic anion. Suitable strong bases for this reaction include metal alkoxides, such as sodium methoxide, sodium ethoxide, lithium ethoxide, lithium t-butoxide, and potassium t-butoxide; sodium hydride; alkyllithiums, such as n-butyllithium, t-butyllithium, sec-butyllithium, and methyllithium; and metal amides, such as sodium amide, magnesium diisopropylamide, and lithium diisopropylamide. The preferred base for this transformation is n-butyllithium. This deprotonation reaction is carried out in a dry organic solvent, such as tetrahydrofuran or 1,2-dimethoxyethane, at a temperature of about –25° C.

The benzylic anion is condensed, without isolation, with a benzaldehyde compound of the formula p-R₁(C₆H₄)CHO, wherein R₁ is as defined above. Preferably, about one equivalent of the benzaldehyde is added to the cold solution prepared as described in the preceding paragraph. The resulting diastereomeric mixture of condensation products may be isolated, or preferably used in the next step without isolation.

The condensation product is optionally treated with a base, such as n-butyllithium, and reacted with an acid chloride. Representative acid chlorides include acyl chlorides, such as acetyl chloride and benzoyl chloride; sulfonyl chlorides, such as methanesulfonyl chloride, benzenesulfonyl chloride, 1-butanesulfonyl chloride, ethanesulfonyl chloride, isopropylsulfonyl chloride, and p-toluenesulfonyl chloride; alkoxycarbonyl chlorides, such as methoxycarbonyl chloride and benzyloxycarbonyl chloride; and dialkylaminocarbonyl chlorides, such as N,N-dimethylaminocarbonyl chloride; preferably a sulfonyl chloride. The acid chloride is added to the cold reaction mixture, then the resulting mixture is allowed to warm to room temperature. Preferably, methanesulfonyl chloride is added to the reaction mixture shortly after formation of the condensation product, which eliminates the need to add additional base.

The resulting intermediate ester is reacted with a second strong base to produce the E and Z, styryl sulfoxides, formula II compounds where $R_1$, $R_2$, and $R_3$ are as defined above. Representative second strong bases for this elimination reaction include metal alkoxides, such as sodium methoxide, sodium ethoxide, lithium ethoxide, lithium t-butoxide, and potassium t-butoxide; sodium hydride; alkyllithiums, such as n-butyllithium, t-butyllithium, sec-butyllithium, and methyllithium; and metal amides, such as sodium amide, magnesium diisopropylamide, and lithium diisopropylamide. The preferred base for this transformation is potassium t-butoxide. Preferably, a 20% excess, such as 1.2 equivalents, of the second base are added. Generally, this reaction is carried out at a temperature of about 15° C. to about room temperature, preferably at room temperature.

The intermediate styryl sulfoxides are useful for the synthesis of 2-arylbenzo[b]thiophenes as shown in Scheme 4.

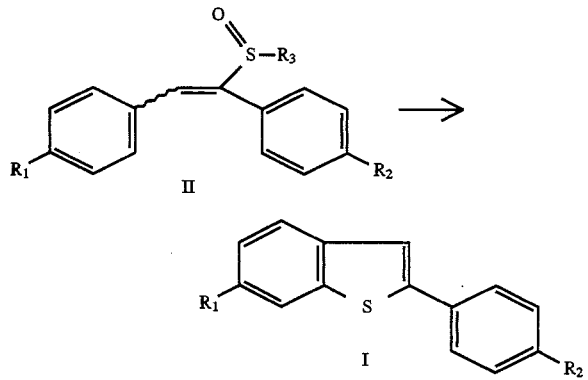

Scheme 4

Generally, the intermediate styryl sulfoxide compounds are heated and treated with acid catalysts to produce the formula I compounds. Suitable acid catalysts for this reaction include Lewis acids or Brønsted acids. Representative Lewis acids include zinc chloride, zinc iodide, aluminum chloride, and aluminum bromide. Representative Brønsted acids include inorganic acids, such as sulfuric and phosphoric acids; carboxylic acids, such as acetic and trifluoroacetic acids; sulfonic acids, such as methanesulfonic, benzenesulfonic, 1-naphthalenesulfonic, 1-butanesulfonic, ethanesulfonic, 4-ethylbenzenesulfonic, 1-hexanesulfonic, 1,5-naphthalenedisulfonic, 1-octanesulfonic, camphorsulfonic, trifluoromethanesulfonic, and p-toluenesulfonic acids; and polymeric arylsulfonic acids, such as Nafion®, Amberlyst®, or Amberlite®. The more preferred acid catalysts are sulfonic acids, such as methanesulfonic acid, benzene-sulfonic acid, camphorsulfonic, and p-toluenesulfonic acid. The most preferred acid catalyst is p-toluenesulfonic acid. Typically, a solution of the acid catalyst in organic solvent, such as toluene, benzene, xylene, or a high-boiling halogenated hydrocarbon solvents, such as 1,1,2-trichloro-ethane, is heated to about 80° to about 140° C., and treated with a solution of the styryl sulfoxide in the same solvent. An excess amount of the acid catalyst is used, preferably two equivalents of the acid. For best results, the final concentration of the starting compound is about 0.01M to about 0.2M, preferably 0.05M. Furthermore, best yields are obtained when the styryl sulfoxide is slowly added to the heated acid solution over a period of about 20 minutes to about three hours. For best results, residual water is removed from the reaction solution by the use of a Dean-Stark trap or Soxhlet extractor, and the reaction is purged with purified nitrogen.

The formula I compounds are useful as intermediates in the synthesis of a series of 3-aroyl-2-arylbenzo[b] thiophenes. U.S. Pat. Nos. 4,133,814 and 4,418,068, which are incorporated herein by reference, described these 3-aroyl-2-arylbenzo[b]thiophenes, as well as methods for their preparation from the formula I compounds. An improved synthesis of a group of these 3-aroyl-2-arylbenzo [b]thiophenes from the formula I compounds, wherein $R_1$ and $R_2$ are hydrogen, $C_1$–$C_4$ alkoxy, or arylalkoxy, is outlined in Scheme 5.

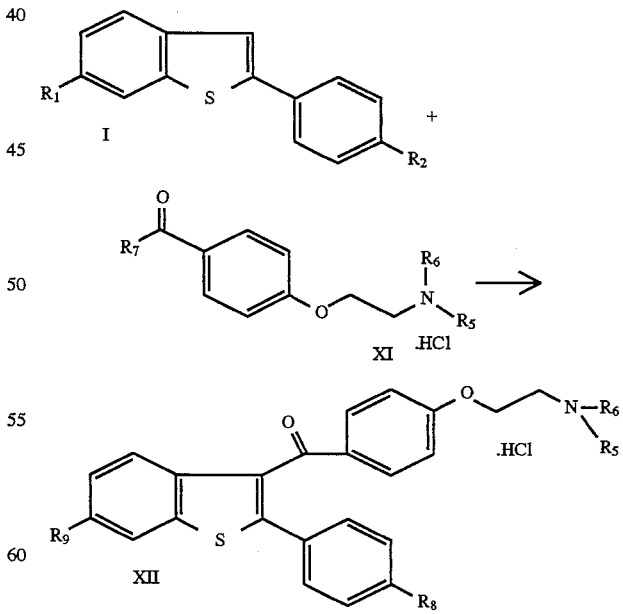

Scheme 5

The benzothiophene Formula I compound, wherein $R_1$ and $R_2$ are hydrogen, $C_1$–$C_4$ alkoxy, or arylalkoxy, is acylated with the formula XI compound, wherein $R_7$ is chloro or hydroxy, in the presence of boron trichloride or boron tribromide; boron trichloride is preferred. The reaction can be carried out in a variety of organic solvents, such as chloroform, methylene chloride, 1,2-dichloroethane, 1,2,3-dichloropropane, 1,1,2,2-tetra-chloroethane, 1,2-dichlorobenzene, chlorobenzene, and fluorobenzene. The preferred solvent for this synthesis is 1,2-dichloroethane. The reaction is carried out at a temperature of about −10° C. to about 25° C., preferably at 0° C. The reaction is best carried out at a concentration of the benzothiophene formula I compound of about 0.2M to about 1.0 M. The acylation reaction is generally complete after about two hours to about eight hours.

When $R_1$ and/or $R_2$ is a $C_1$–$C_4$ alkoxy or arylalkoxy group, the acylated benzothiophene, is converted to a formula XI compound wherein $R_8$ and/or $R_9$ are hydroxy, without isolation of the product from the acylation reaction. This conversion is performed by adding additional boron trihalide or boron tribromide and heating the reaction mixture. Preferably, two to five molar equivalents of boron trihalide are added to the reaction mixture, most preferably three molar equivalents. This reaction is carried out at a temperature of about 25° C. to about 40° C., preferably at 35° C. The reaction is generally complete after about 4 to 48 hours.

The acylation reaction or acylation/dealkylation reaction is quenched with an alcohol or a mixture of alcohols. Suitable alcohols for use in quenching the reaction include methanol, ethanol, and isopropanol. Preferably, the acylation/dealkylation reaction mixture is added to a 95:5 mixture of ethanol and methanol (3A ethanol). The 3A ethanol can be at room temperature or heated to reflux, preferably at reflux. When the quench is performed in this manner, the Formula XII compound conveniently crystallizes from the resulting alcoholic mixture. Generally, 1.25 mL to 3.75 mL of alcohol per millimole of the benzothiophene starting material are used.

The following examples further illustrate the present invention. The examples are not intended to be limiting to the scope of the invention in any respect, and should not be so construed. All experiments were run under positive pressure of dry nitrogen. All solvents and reagents were used as obtained. The percentages are generally calculated on a weight (w/w) basis; except for high performance liquid chromatography (HPLC) solvents which are calculated on a volume (v/v) basis. Proton nuclear magnetic resonance ($^1$H NMR) spectra and $^{13}$C nuclear magnetic resonance spectra ($^{13}$C NMR) were obtained on a Bruker AC-300 FTNMR spectrometer at 300.135 MHz or a GE QE-300 spectrometer at 300.15 MHz. Silica-gel flash chromatography was performed as described by Still et al. using Silica Gel 60 (230–400 mesh, E. Merck). Still et al., *J. Org. Chem.*, 43, 2923 (1978). Elemental analyses for carbon, hydrogen, and nitrogen were determined on a Control Equipment Corporation 440 Elemental Analyzer. Elemental analyses for sulfur were determined on a Brinkman Colorimetric Elemental Analyzer. Melting points were determined in open glass capillaries on a Mel-Temp II melting point apparatus or a Mettler FP62 Automatic instrument, and are uncorrected. Field desorption mass spectra (FDMS) were obtained using a Varian Instruments VG 70-SE or VG ZAB-3F mass spectrometer. High resolution free atom bombardment mass spectra (FABMS) were obtained using a Varian Instruments VG ZAB-2SE mass spectrometer.

The in situ yields of 6-methoxy-2-(4-methoxyphenyl)benzo[b]thiophene were determined by high performance liquid chromatography (HPLC) in comparison to an authentic sample of this compound prepared by published synthetic routes. See U.S. Pat. No. 4,133,814. Generally, samples of the reaction mixture was diluted with acetonitrile and the diluted sample assayed by HPLC using a Zorbax RX-C8 column (4.6 mm×25 cm) with UV detection (280 nm). The following linear-gradient solvent system was used for this analysis:

| Gradient Solvent System | | |
|---|---|---|
| Time (min) | A (%) | B (%) |
| 0 | 50 | 50 |
| 2 | 50 | 50 |
| 20 | 20 | 80 |
| 35 | 20 | 80 |
| 37 | 50 | 50 |
| 45 | 50 | 50 |

A: 0.01 M aqueous sodium phosphate (pH 2.0)
B: acetonitrile

The amount (percentages) of 6-hydroxy-2-(4-hydroxyphenyl)-3-[4-(2-piperidinoethoxy)benzoyl]benzo[b]thiophene hydrochloride in the crystalline material (potency) was determined by the following method. A sample of the crystalline solid (5 mg) was weighed into a 100-mL volumetric flask, and dissolved in a 70/30 (v/v) mixture of 75 mM potassium phosphate buffer (pH 2.0) and acetonitrile. An aliquot of this solution (10 µL) was assayed by high performance liquid chromatography, using a Zorbax Rx-C8 column (25 cm×4.6 mm ID, 5µ particle) and UV detection (280 nm). The following gradient solvent system was used:

| Gradient Solvent System (Potency) | | |
|---|---|---|
| Time (min) | A (%) | B (%) |
| 0 | 70 | 30 |
| 12 | 70 | 30 |
| 14 | 25 | 75 |
| 16 | 70 | 30 |
| 25 | 70 | 30 |

A: 73 mM $KH_2PO_4$ buffer (pH 2.0)
B: acetonitrile

The percentage of 6-hydroxy-2-(4-hydroxyphenyl)-3-[4-(2-piperidinoethoxy)benzoyl]benzo[b]thiophene hydrochloride in the sample was calculated using the peak area, slope (m), and intercept (b) of the calibration curve with the following equation:

$$\% \text{ potency} = \frac{\text{peak area} - b}{m} \times \frac{\text{sample volume (mL)}}{\text{sample weight (mg)}}$$

The amount (percentage) of solvent, such as 1,2-dichloroethane, present in the crystalline material was determined by gas chromatography. A sample of the crystalline solid (50 mg) was weighed into a 10-mL volumetric flask, and dissolved in a solution of 2-butanol (0.025 mg/mL) in dimethylsulfoxide. A sample of this solution was analyzed on a gas chromatograph using a DB Wax column (30 m×0.53 mm ID, 1µ particle), with a column flow of 10 mL/min and flame ionization detection. The column temperature was heated from 35° C. to 230° C. over a 12 minute period. The amount of solvent was determined by comparison to the internal standard (2-butanol).

EXAMPLE 1

E-t-Butyl 4,4'-Dimethoxystilbenyl Sulfoxide

A. Preparation of E-t-Butyl 4,4'-Dimethoxystilbenyl Sulfide

A solution of desoxyanisoin (12.82 g) in tetrahydrofuran (100 mL) was treated with titanium (IV) chloride (10.43 g). During the dropwise addition of titanium (IV) chloride, the reaction mixture was cooled to maintain the temperature below 35° C. Upon complete addition, the resulting mixture was stirred at 30° C. After an additional 30 minutes, this mixture was treated with a solution of 2-methyl-2-propanethiol (6.76 mL) and triethylamine (16.70 mL) in tetrahydrofuran (15 mL). The resulting mixture was stirred at 50° C. After two hours, the mixture was added to ten percent sodium carbonate (500 mL). The resulting mixture was extracted with methylene chloride. The combined methylene chloride extracts were dried over magnesium sulfate, filtered, and concentrated in vacuo to give 17.2 g of an oil, which crystallized upon cooling to room temperature. This crystalline material was recrystallized from hot ethanol to give 12.3 g of the title compound. Melting point 71°–73° C.

Analysis calculated for $C_{20}H_{24}O_2S$: C, 73.13; H, 7.36; S, 9.76. Found: C, 73.37; H, 7.51; S, 9.87.

B. Preparation of E-t-Butyl 4,4'-Dimethoxystilbenyl Sulfoxide

The crystalline compound prepared as described in Example 1A was dissolved in toluene (150 mL), and the resulting solution cooled to about −20° C. The cold solution was treated with peracetic acid (32% w/w in dilute acetic acid, 1.24 g) over ten minutes. The resulting mixture was extracted with saturated sodium sulfite and brine. The organic phase was concentrated in vacuo. The residue was recrystallized from ethyl acetate/heptane to give 14.11 g of the title compound. Melting point 104° C. (dec).

Analysis calculated for $C_{20}H_{24}O_3S$: C, 69.74; H, 7.02; S, 9.31. Found: C, 69.47; H, 7.04; S, 9.54.

EXAMPLE 2

Z-t-Butyl 4,4'-Dimethoxystilbenyl Sulfoxide

A. Preparation of t-Butyl 4-Methoxybenzyl Sulfide

A mixture of 4-methoxybenzyl alcohol (10.13 g) and zinc iodide (11.7 g) in 1,2-dichloroethane (120 mL) was treated with 2-methyl-2-propanethiol (9.92 mL) in one portion. The resulting mixture was stirred at room temperature. After about 18 hours, the reaction was diluted with water (100 mL) and methylene chloride (100 mL). The organic phase was removed, dried over magnesium sulfate, filtered, and concentrated in vacuo to give 14.4 g of an oil.

$^1$H NMR (CDCl$_3$): δ 7.28 (d, 2H), 6.85 (d, 2H), 3.77 (s, 3H), 3.73 (s, 2H), 1.36 (s, 9H).

$^{13}$C NMR (CDCl$_3$): δ 130, 114, 56, 35, 32.

Analysis calculated for $C_{12}H_{18}OS$: C, 68.52; H, 8.63. Found: C, 68.8; H, 8.67.

B. Preparation of Z-t-Butyl 4,4'Dimethoxystilbenyl Sulfide

A solution of the compound prepared as described in Example 2A (2.51 g) in tetrahydrofuran (50 mL) was cooled to about −20° C. This cold solution was treated with a solution of n-butyllithium in hexane (1.6M, 7.47 mL) over ten minutes. The resulting solution was allowed to warm to about 0° C. over 35 minutes. This cold solution was treated with p-anisaldehyde (1.46 mL). After an additional 15 minutes, the reaction solution was treated with methanesulfonyl chloride (0.95 mL). The resulting reaction was allowed to warm to room temperature. After an additional 45 minutes, the reaction mixture was treated with a solution of potassium t-butoxide in tetrahydrofuran (1.0M, 12.0 mL). After an additional 45 minutes, the reaction was quenched by the addition of 1N hydrochloric acid (12.0 mL). The organic phase was separated, dried over magnesium sulfate, filtered, and concentrated to an oil (4.4 g).

$^1$H NMR (CDCl$_3$): δ 7.95 (d, H), 7.05 (s, H), 6.9 (d, H), 6.8 (dd, 2H), 3.75 (s, 3H), 0.95 (s, 9H).

$^{13}$C NMR (CDCl$_3$): δ 153, 139, 137, 114, 56, 32.

C. Preparation of Z-t-Butyl 4,4'-Dimethoxystilbenyl Sulfoxide

The compound from Example 2B was converted to the title compound using the procedure substantially as described in Example 1B.

$^1$H NMR (CDCl$_3$): δ 7.61 (d, H), 7.56 (d, H), 7.1 (s, H), 6.9 (dd, 2H), 3.83 (s, 3H), 1.05 (s, 9H).

$^{13}$C NMR (CDCl$_3$): δ 142, 132.5, 131, 118, 117, 56, 24.

Analysis calculated for $C_{20}H_{24}O_3S$: C, 69.74; H, 7.02. Found: C, 69.98; H, 6.94.

EXAMPLE 3

E and Z-t-Butyl 4,4'-Dimethoxystilbenyl Sulfoxide

A. Preparation of t-Butyl 4-Methoxybenzyl Sulfide

A mixture of 4-methoxybenzyl alcohol (10.13 g) and zinc iodide (11.7 g) in 1,2-dichloroethane (120 mL) was treated with 2-methyl-2-propanethiol (9.92 mL) in one portion. The resulting mixture was stirred at room temperature. After about 18 hours, the reaction was diluted with water (100 mL) and methylene chloride (100 mL). The organic phase was removed, dried over magnesium sulfate, filtered, and concentrated in vacuo to give 14.4 g of an oil.

$^1$H NMR (CDCl$_3$): δ 7.28 (d, 2H), 6.85 (d, 2H), 3.77 (s, 3H), 3.73 (s, 2H), 1.36 (s, 9H).

$^{13}$C NMR (CDCl$_3$): δ 130, 114, 56, 35, 32.

Analysis calculated for $C_{12}H_{18}OS$: C, 68.52; H, 8.63. Found: C, 68.8; H, 8.67.

B. Preparation of t-Butyl 4-Methoxybenzyl Sulfoxide

A solution of the compound prepared as described in Example 3A (14.4 g) in 1,2-dichloroethane (50 mL) was cooled to about 5° C. and the cold solution treated with peracetic acid (32% w/w in dilute acetic acid, 14.2 mL) over 30 minutes. Upon complete addition of the peracetic acid, the reaction was treated with brine and sodium bicarbonate. The organic phase was removed, dried over magnesium sulfate, filtered, and concentrated to a yellow precipitate. This residue was treated with hexane (100 mL) and the resulting mixture stirred at room temperature. After about 18 hours, the mixture was filtered and the solids washed with hexane (100 mL). The solid material was dried in vacuo to give 14.07 g of the title compound. Melting point 124°–126° C.

$^1$H NMR (CDCl$_3$): δ 7.26 (d, 2H), 6.89 (d, 2H), 3.79 (d, H), 3.78 (s, 3H), 3.58 (d, H), 1.3 (s, 9H).

$^{13}$C NMR (CDCl$_3$): δ 132, 114, 56, 53, 23.

Analysis calculated for C$_{12}$H$_{18}$O$_2$S: C, 63.68; H, 8.02. Found: C, 63.72; H, 7.93.

C. Preparation of E and Z-t-Butyl 4,4'-Dimethoxystilbenyl Sulfoxide

A solution of the compound prepared as described in Example 3B (10.0 g) in tetrahydrofuran (140 mL) was cooled to about −30° to −25° C. (dry ice/acetone bath). This cold solution was treated with n-butyllithium in cyclohexane (1.6M, 27.65 mL) over 25 minutes. After stirring for 35 minutes, the reaction mixture was treated with p-anisaldehyde (5.4 mL). The dry ice/acetone bath was removed and the reaction allowed to warm to about 20° C. This mixture was treated with methanesulfonyl chloride (3.5 mL). The temperature of the reaction rose from about 20° to about 35° C. upon addition of the methanesulfonyl chloride. The mixture was cooled to about 25° C., then treated with potassium t-butoxide in tetrahydrofuran (1M, 50.9 mL). After stirring for an additional 35 minutes, the reaction was treated with 1N hydrochloric acid (51.0 mL). The phases were separated, and the organic layer dried over magnesium sulfate, filtered, and concentrated to an oil (16.67 g). This material was used in the next step without further purification. The carbon and proton NMR spectra were similar to that obtained for the compound prepared as described in Examples 1 and 2.

EXAMPLE 4

Z-t-Butyl 4,4'-Dimethoxystilbenyl Sulfoxide

A solution of the compound prepared as described in Example 3B (3.0 g) in tetrahydrofuran (40 mL) was cooled to about −15° C. This cold solution was treated with n-butyllithium in cyclohexane (1.6M, 8.3 mL) over 15 minutes. After stirring for ten minutes, the reaction mixture was warmed to 0° C., and treated with p-anisaldehyde (1.61 mL). The ice bath was removed and the reaction allowed to warm to about room temperature. This mixture was treated with acetyl chloride (0.95 mL). After about one hour, the reaction mixture was treated with potassium t-butoxide in tetrahydrofuran (1M, 16.0 mL). After stirring for an additional 1.5 hours, the reaction was treated with 1N hydrochloric acid (17.0 mL). The phases were separated, and the organic layer dried over magnesium sulfate, filtered, and concentrated to an oil (5.26 g). This material was used without further purification. The carbon and proton NMR spectra were similar to that obtained for the compound prepared as described in Example 2.

EXAMPLE 5

6-Methoxy-2-(4-methoxyphenyl)benzo[b]thiophene

A solution of p-toluenesulfonic acid monohydrate (2.25 g) in toluene (60 mL) was heated to reflux, and water was removed by allowing it to collect in a Dean-Stark trap. Using a nitrogen gas purge vented through the top of the condenser, a solution of the compound prepared as described in Example 1 (2.04 g) in toluene (33 mL) was added to the refluxing acid solution over 1.5 hours. The resulting mixture was cooled to about 5° C. under the nitrogen purge, then treated with water (8 mL). The resulting slurry was stirred for three hours. The slurry was filtered, and the crystalline product washed with water (8 mL) and acetone (8 mL). The crystalline product was dried in vacuo at 40° C. for about 18 hours to give 1.30 g of the title compound as a light tan solid.

This compound was identical to the compound prepared by a published route. Melting Point 196°–199° C.

EXAMPLE 6

6-Methoxy-2-(4-methoxyphenyl)benzo[b]thiophene

A solution of p-toluenesulfonic acid monohydrate (2.49 g) in toluene (108 mL) was heated to reflux, and water was removed by allowing it to collect in a Dean-Stark trap. A solution of the compound prepared as described in Example 1 (9.00 g) in toluene (32 mL) was added to the refluxing acid solution over six hours. Upon complete addition, absolute ethanol (35 mL) was added to the reaction solution, and the resulting mixture was allowed to cool to room temperature. After about 18 hours, a precipitate was isolated by filtration. This precipitate was washed with toluene/absolute ethanol (4:1, 29 mL), and dried in vacuo at 40° C. for about 18 hours to give 4.86 g of a solid. This compound was identical to the compound prepared by a published route. Melting point 199°–200° C.

EXAMPLE 7

6-Hydroxy-2-(4-hydroxyphenyl)-3-[4-(2-piperidinoethoxy)benzoyl]benzo[b]thiophene Hydrochloride 1,2-Dichloroethane Solvate

A. Preparation of Ethyl 4-(2-Piperidinoethoxy)benzoate

A mixture of ethyl 4-hydroxybenzoate (8.31 g), 1-(2-chloroethyl)piperidine monohydrochloride (10.13 g), potassium carbonate (16.59 g), and methyl ethyl ketone (60 mL) was heated to 80° C. After one hour, the mixture was cooled to about 55° C. and treated with additional 1-(2-chloroethyl)piperidine monohydrochloride (0.92 g). The resulting mixture was heated to 80° C. The reaction was monitored by thin layer chromatography (TLC), using silica-gel plates and ethyl acetate/acetonitrile/triethylamine (10:6:1, v/v). Additional portions of 1-(2-chloroethyl)piperidine hydrochloride are added until the starting 4-hydroxybenzoate ester is consumed. Upon complete reaction, the reaction mixture was treated with water (60 mL) and allowed to cool to room temperature. The aqueous layer was discarded and the organic layer concentrated in vacuo at 40° C. and 40 mm Hg. The resulting oil was used in the next step without further purification.

B. Preparation of 4-(2-Piperidinoethoxy)benzoic Acid Hydrochloride

A solution of the compound prepared as described in Example 7A (about 13.87 g) in methanol (30 mL) was treated with 5N sodium hydroxide (15 mL), and heated to 40° C. After 4½ hours, water (40 mL) was added. The resulting mixture was cooled to 5°–10° C., and concentrated hydrochloric acid (18 mL) was added slowly. The title compound crystallized during acidification. This crystalline product was collected by filtration, and dried in vacuo at 40°–50° C. to give 83% yield of the title compound. Melting point 270°–271° C.

C. Preparation of 4-(2-Piperidinoethoxy)benzoyl Chloride Hydrochloride

A solution of the compound prepared as described in Example 7B (30.01 g) and dimethylformamide (2 mL) in methylene chloride (500 mL) was treated with oxalyl chloride (10.5 mL) over a 30–35 minute period. After stirring for about 18 hours, the reaction was assayed for completion by HPLC analysis. Additional oxalyl chloride may be added to the reaction if the starting carboxylic acid is present. Upon completion, the reaction solution was evaporated to dryness in vacuo. The residue was dissolved in methylene chloride (200 mL), and the resulting solution evaporated to dryness. This dissolution/evaporation procedure was repeated to give the title compound as a solid. The title compound may be stored as a solid or as a 0.2M solution in methylene chloride (500 mL).

D. Preparation of 6-Hydroxy-2-(4-hydroxyphenyl)-3-[4-(2-piperidinoethoxy)benzoyl]benzo[b]thiophene Hydrochloride 1,2-Dichloroethane Solvate A mixture of the compound prepared as described in Example 5 or 6 (2.92 g), the compound prepared as described in Example 7C (3.45 g), and 1,2-dichloroethane (52 mL) was cooled to about 0° C. Boron trichloride gas was condensed into a cold graduated cylinder (2.8 mL), and added to the cold mixture described above. After eight hours at 0° C., the reaction mixture was treated with additional boron trichloride (2.8 mL). The resulting solution was heated to 35° C. After 16 hours, the reaction was complete.

Methanol (30 mL) was treated with the reaction mixture from above over a 20-minute period, causing the methanol to reflux. The resulting slurry was stirred at 25° C. After one hour, the crystalline product was filtered, washed with cold methanol (8 mL), and dried at 40° C. in vacuo to give 5.14 g of the title compound. Melting point 225° C.

Potency: 86.8%
1,2-Dichloroethane: 6.5% (gas chromatography)

We claim:

1. A compound of the formula

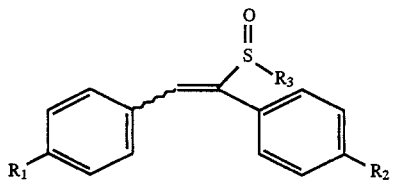

II wherein:

$R_1$ is hydrogen, $C_1$–$C_4$ alkoxy, arylalkoxy, halo, or amino;
$R_2$ is hydrogen, $C_1$–$C_4$ alkoxy, arylalkoxy, halo, or amino; and
$R_3$ is a thermally-labile or acid-labile $C_2$–$C_{10}$ alkyl, $C_4$–$C_{10}$ alkenyl, or aryl($C_1$–$C_{10}$ alkyl) group,
provided $R_1$ and $R_2$ are not both hydrogen when $R_3$ is $C_2$–$C_{10}$ alkyl or aryl($C_1$–$C_{10}$ alkyl), and $R_1$ is not $C_1$–$C_4$ alkoxy when $R_2$ is hydrogen and $R_3$ is $C_2$–$C_{10}$ alkyl.

2. A compound as claimed in claim 1 wherein:
$R_1$ is hydrogen, $C_1$–$C_4$ alkoxy, or arylalkoxy; and
$R_2$ is hydrogen, $C_1$–$C_4$ alkoxy, or arylalkoxy.

3. A compound as claimed in claim 2 wherein $R_3$ is a thermally-labile or acid-labile $C_2$–$C_{10}$ alkyl or aryl($C_1$–$C_{10}$ alkyl) group.

4. A compound as claimed in claim 3 wherein $R_3$ is a thermally-labile or acid-labile $C_2$–$C_{10}$ alkyl group.

5. A compound as claimed in claim 4 wherein:
$R_1$ is hydrogen or $C_1$–$C_4$ alkoxy; and
$R_2$ is hydrogen or $C_1$–$C_4$ alkoxy.

6. A compound as claimed in claim 5 wherein $R_1$ and $R_2$ are $C_1$–$C_4$ alkoxy.

7. A compound as claimed in claim 6 wherein $R_3$ is t-butyl.

8. A compound as claimed in claim 5 wherein $R_1$ and $R_2$ are methoxy.

9. A compound as claimed in claim 1 of the formula

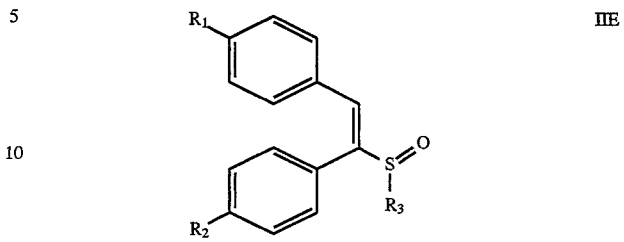

IIE wherein:

$R_1$ is hydrogen, $C_1$–$C_4$ alkoxy, arylalkoxy, halo, or amino;
$R_2$ is hydrogen, $C_1$–$C_4$ alkoxy, arylalkoxy, halo, or amino; and
$R_3$ is a thermally-labile or acid-labile $C_2$–$C_{10}$ alkyl, $C_4$–$C_{10}$ alkenyl, or aryl($C_1$–$C_{10}$ alkyl) group,
provided $R_1$ and $R_2$ are not both hydrogen when $R_3$ is $C_2$–$C_{10}$ alkyl or aryl($C_1$–$C_{10}$ alkyl), and $R_1$ is not $C_1$–$C_4$ alkoxy when $R_2$ is hydrogen and $R_3$ is $C_2$–$C_{10}$ alkyl.

10. A compound as claimed in claim 9 wherein $R_1$ and $R_2$ are methoxy, and $R_3$ is t-butyl.

11. A compound as claimed in claim 1 of the formula

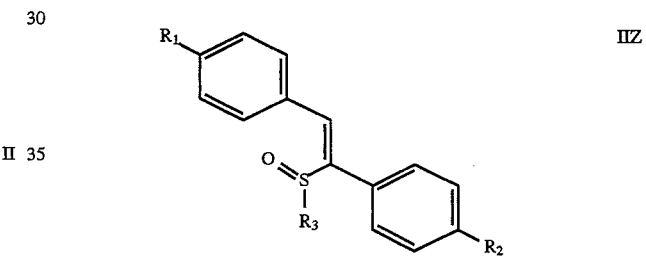

IIZ wherein:

$R_1$ is hydrogen, $C_1$–$C_4$ alkoxy, arylalkoxy, halo, or amino;
$R_2$ is hydrogen, $C_1$–$C_4$ alkoxy, arylalkoxy, halo, or amino; and
$R_3$ is a thermally-labile or acid-labile $C_2$–$C_{10}$ alkyl, $C_4$–$C_{10}$ alkenyl, or aryl($C_1$–$C_{10}$ alkyl) group,
provided $R_1$ and $R_2$ are not both hydrogen when $R_3$ is $C_2C_{10}$ alkyl or aryl($C_1$–$C_{10}$ alkyl), and $R_1$ is not $C_1$–$C_4$ alkoxy when $R_2$ is hydrogen and $R_3$ is $C_2$–$C_{10}$ alkyl.

12. A compound as claimed in claim 11 wherein $R_1$ and $R_2$ are methoxy, and $R_3$ is t-butyl.

13. A compound of the formula

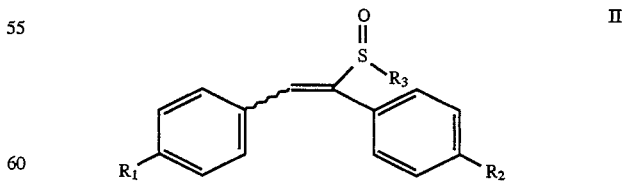

II wherein:

$R_1$ is hydrogen, $C_1$–$C_4$ alkoxy, arylalkoxy, halo, or amino;
$R_2$ is $C_1$–$C_4$ alkoxy, arylalkoxy, halo, or amino; and
$R_3$ is a thermally-labile or acid-labile $C_2$–$C_{10}$ alkyl, $C_4$–$C_{10}$ alkenyl, or aryl($C_1$–$C_{10}$ alkyl) group.

14. A compound as claimed in claim 13 of the formula

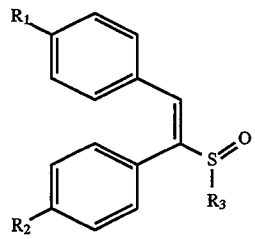

IIE wherein:

$R_1$ is hydrogen, $C_1$–$C_4$ alkoxy, arylalkoxy, halo, or amino;

$R_2$ is $C_1$–$C_4$ alkoxy, arylalkoxy, halo, or amino; and $R_3$ is a thermally-labile or acid-labile $C_2$–$C_{10}$ alkyl, $C_4$–$C_{10}$ alkenyl, or aryl($C_1$–$C_{10}$ alkyl) group.

15. A compound as claimed in claim 13 of the formula

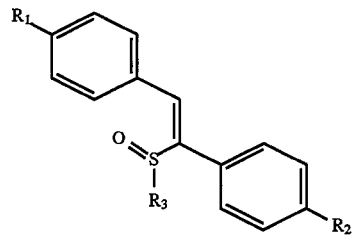

IIZ wherein:

$R_1$ is hydrogen, $C_1$–$C_4$ alkoxy, arylalkoxy, halo, or amino;

$R_2$ is $C_1$–$C_4$ alkoxy, arylalkoxy, halo, or amino; and $R_3$ is a thermally-labile or acid-labile $C_2$–$C_{10}$ alkyl, $C_4$–$C_{10}$ alkenyl, or aryl($C_1$–$C_{10}$ alkyl) group.

* * * * *

UNITED STATES PATENT AND TRADEMARK OFFICE
CERTIFICATE OF CORRECTION

PATENT NO. : 5,659,087

DATED : August 19, 1997

INVENTOR(S) : James A. Aikins, et al.

It is certified that error appears in the above-identified patent and that said Letters Patent is hereby corrected as shown below:

In Column 12, line 43, please replace the number "73" with the number -- 75 --.

Signed and Sealed this

First Day of September, 1998

Attest:

BRUCE LEHMAN

Attesting Officer

Commissioner of Patents and Trademarks